US011020019B2

(12) United States Patent
DeHennis et al.

(10) Patent No.: US 11,020,019 B2
(45) Date of Patent: Jun. 1, 2021

(54) DYNAMIC AMPLIFIER CHANGE

(71) Applicant: Senseonics, Incorporated, Germantown, MD (US)

(72) Inventors: Andrew DeHennis, Germantown, MD (US); Abhi Chavan, Germantown, MD (US); Eitan Saba-Keren, Germantown, MD (US)

(73) Assignee: Senseonics, Incorporated, Germantown, MD (US)

( * ) Notice: Subject to any disclaimer, the term of this patent is extended or adjusted under 35 U.S.C. 154(b) by 300 days.

(21) Appl. No.: 16/158,605

(22) Filed: Oct. 12, 2018

(65) Prior Publication Data

US 2019/0110713 A1    Apr. 18, 2019

Related U.S. Application Data

(60) Provisional application No. 62/572,174, filed on Oct. 13, 2017.

(51) Int. Cl.
| | | |
|---|---|---|
| *A61B 5/145* | (2006.01) | |
| *A61B 5/1455* | (2006.01) | |
| *A61B 5/07* | (2006.01) | |
| *A61B 5/1459* | (2006.01) | |
| *A61B 5/00* | (2006.01) | |
| *H01Q 1/27* | (2006.01) | |
| *H01Q 7/00* | (2006.01) | |

(52) U.S. Cl.
CPC ............ *A61B 5/076* (2013.01); *A61B 5/0004* (2013.01); *A61B 5/1455* (2013.01); *A61B 5/1459* (2013.01); *A61B 5/14532* (2013.01); *H01Q 1/273* (2013.01); *A61B 5/681* (2013.01); *A61B 2560/0219* (2013.01); *H01Q 7/00* (2013.01)

(58) Field of Classification Search
CPC ....... A61B 5/076; A61B 5/1455; A61B 5/681; A61B 2560/0219
See application file for complete search history.

(56) References Cited

U.S. PATENT DOCUMENTS

| | | |
|---|---|---|
| 6,441,747 B1 | 8/2002 | Khair et al. |
| 8,073,548 B2 | 12/2011 | Colvin, Jr. et al. |
| 9,414,775 B2 | 8/2016 | Colvin, Jr. et al. |
| 9,693,714 B2 | 7/2017 | DeHennis et al. |
| 2012/0071159 A1 | 3/2012 | Akhi et al. |
| 2013/0158376 A1 | 6/2013 | Hayter et al. |

(Continued)

*Primary Examiner* — Eric F Winakur
(74) *Attorney, Agent, or Firm* — Rothwell, Figg, Ernst & Manbeck, P.C.

(57) ABSTRACT

An analyte monitoring system and methods for extending the life of a sensor in an analyte monitoring system. The analyte sensor may include an analyte sensor and a transceiver. The analyte sensor may include an indicator, a detector, and an amplifier. The indicator may be configured to exhibit one or more detectable properties based on an amount or concentration of an analyte in proximity to the indicator. The detector may be configured to detect one or more of the detectable properties and output an analyte signal indicative of the amount or concentration of the analyte in proximity to the indicator. The amplifier may be configured to amplify the analyte signal. The transceiver may be configured to adjust a gain of the amplifier. The transceiver may be configured to additionally or alternatively adjust a drive current of a light source of the analyte sensor.

39 Claims, 9 Drawing Sheets

(56) References Cited

U.S. PATENT DOCUMENTS

| | | |
|---|---|---|
| 2013/0241745 A1 | 9/2013 | Colvin, Jr. et al. |
| 2014/0080225 A1 | 3/2014 | Chodavarapu et al. |
| 2015/0045635 A1 | 2/2015 | Tankiewicz et al. |
| 2016/0374597 A1* | 12/2016 | Stahmann .............. A61B 5/746 600/309 |
| 2017/0027489 A1 | 2/2017 | Mao et al. |

* cited by examiner

| Quantization Level (for Kd=23) | Cal Gain | ADC Noise (STD) | Glucose Level mg/dL | Glucose Error mg/dL |
|---|---|---|---|---|
| 4.55 | 1 | 1.8 | 144 | 9 |
| 4.55 | 1 | 1.8 | 400 | 18 |
| 4.55 | 0 | 0.5 | 144 | 3 |
| 4.55 | 0 | 0.5 | 400 | 6 |

DYNAMIC AMPLIFIER CHANGE

CROSS-REFERENCE TO RELATED APPLICATION

The present application claims the benefit of priority to U.S. Provisional Application Ser. No. 62/572,174, filed on Oct. 13, 2017, which is incorporated herein by reference in its entirety.

BACKGROUND

Field of Invention

The present invention relates to extending the life of an analyte sensor in an analyte monitoring system while maintaining accuracy. More specifically, aspects of the present invention may relate to utilizing dynamic signal amplification to compensate for chemical modulation loss.

Discussion of the Background

The prevalence of diabetes mellitus continues to increase in industrialized countries, and projections suggest that this figure will rise to 4.4% of the global population (366 million individuals) by the year 2030. Glycemic control is a key determinant of long-term outcomes in patients with diabetes, and poor glycemic control is associated with retinopathy, nephropathy and an increased risk of myocardial infarction, cerebrovascular accident, and peripheral vascular disease requiring limb amputation. Despite the development of new insulins and other classes of antidiabetic therapy, roughly half of all patients with diabetes do not achieve recommended target hemoglobin A1c (HbA1c) levels <7.0%.

Frequent self-monitoring of blood glucose (SMBG) is necessary to achieve tight glycemic control in patients with diabetes mellitus, particularly for those requiring insulin therapy. However, current blood (finger-stick) glucose tests are burdensome, and, even in structured clinical studies, patient adherence to the recommended frequency of SMBG decreases substantially over time. Moreover, finger-stick measurements only provide information about a single point in time and do not yield information regarding intraday fluctuations in blood glucose levels that may more closely correlate with some clinical outcomes.

Continuous glucose monitors (CGMs) have been developed in an effort to overcome the limitations of finger-stick SMBG and thereby help improve patient outcomes. These systems enable increased frequency of glucose measurements and a better characterization of dynamic glucose fluctuations, including episodes of unrealized hypoglycemia. Furthermore, integration of CGMs with automated insulin pumps allows for establishment of a closed-loop "artificial pancreas" system to more closely approximate physiologic insulin delivery and to improve adherence.

Monitoring real-time analyte measurements from a living body via wireless analyte monitoring sensor(s) may provide numerous health and research benefits. There is a need to enhance such analyte monitoring systems via innovations.

SUMMARY

Aspects of the present invention may relate to extend the life of a sensor in an analyte monitoring system, while maintaining accuracy. Some embodiments may utilize dynamic signal amplification to compensate for chemical modulation loss. By adapting the electrical gain, to the degrading chemical fluorescent light, an analyte monitoring system may continue sensing analyte successfully, for a longer period of time since implant or insertion.

One aspect of the invention may provide an analyte monitoring system including an analyte sensor and a transceiver. The analyte sensor may include an indicator, a detector, and an amplifier. The indicator may be configured to exhibit one or more detectable properties based on an amount or concentration of an analyte in proximity to the indicator. The detector may be configured to detect one or more of the detectable properties and output an analyte signal indicative of the amount or concentration of the analyte in proximity to the indicator. The amplifier may be configured to amplify the analyte signal. The transceiver may be configured to adjust a gain of the amplifier.

In some embodiments, the analyte sensor may further include an analog-to-digital converter (ADC) configured to quantize the amplified analyte signal. In some embodiments, adjusting the gain of the amplifier may include increasing the gain of the amplifier. In some embodiments, the analyte sensor may further include a light source configured to irradiate the indicator with excitation light. In some embodiments, the transceiver may be further configured to adjust a drive current of the light source.

In some embodiments, the transceiver may be further configured to determine whether one or more initial conditions are met. In some embodiments, determining whether the one or more initial conditions are met may include calculating a responsivity and determining whether the calculated responsivity is below a responsivity threshold. In some embodiments, the responsivity may be the responsiveness of the indicator of the analyte sensor to changes in the amount or concentration of the analyte in proximity to the indicator. In some embodiments, determining whether the one or more initial conditions are met may further include determining one or more of (i) whether a first threshold amount of time has passed since implantation or insertion of the analyte sensor, (ii) whether a second threshold amount of time has passed since a previous adjustment of the gain of the amplifier, and (iii) whether the gain of the amplifier has not been adjusted since the analyte sensor was implanted or inserted. In some embodiments, the transceiver may be further configured to determine that the one or more initial conditions are met if the transceiver determines that (1) the first threshold amount of time has passed since implantation or insertion of the analyte sensor, (2) the gain of the amplifier has not been adjusted since the analyte sensor was implanted or inserted or the second threshold amount of time has passed since the previous adjustment of the gain of the amplifier, and (3) the calculated responsivity is below the responsivity threshold. In some embodiments, the transceiver may be further configured to, if the transceiver determines that the one or more initial conditions are met, determine whether one or more pre-converge conditions are met.

In some embodiments, the transceiver may be further configured to determine whether one or more pre-converge conditions are met. In some embodiments, determining whether the one or more pre-converge conditions are met may include determining one or more of (i) whether a level of a battery of the transceiver is above a battery threshold, (ii) whether a rate of change of the amount or concentration of the analyte in proximity to the indicator is below an analyte rate of change threshold, (iii) whether the amount or concentration of the analyte in proximity to the indicator is within an analyte level range, (iv) whether a rate of change of a temperature of the analyte sensor is below a temperature rate of change threshold, (v) whether the temperature of the analyte sensor is within a temperature range, (vi) whether a time of the transceiver is within a time range, (vii) whether there were any ambient light alarms during the past hour, and (viii) whether there are any active ambient light alarms. In some embodiments, the transceiver may be further configured to determine that the one or more pre-converge conditions are met if the transceiver determines that (i) the level of the battery of the transceiver is above the battery threshold, (ii) the rate of change of the amount or concentration of the analyte in proximity to the indicator is below the analyte rate of change threshold, (iii) the amount or concentration of the analyte in proximity to the indicator is within the analyte level range, (iv) the rate of change of the temperature of the analyte sensor is below the temperature rate of change threshold, (v) the temperature of the analyte sensor is within the temperature range, (vi) the time of the transceiver is within the time range, (vii) there were no ambient light alarms during the past hour, and (viii) there are no active ambient light alarms. In some embodiments, the transceiver may be further configured to adjust the gain of the amplifier only if the transceiver determines that the one or more pre-converge conditions are met.

In some embodiments, adjusting the gain of the amplifier may include calculating a new gain for the amplifier of the analyte sensor and changing the gain of the amplifier to the calculated new gain. In some embodiments, adjusting the gain of the amplifier may further include building a calibration buffer. In some embodiments, the analyte sensor may further include an analog-to-digital converter (ADC) configured to quantize the amplified analyte signal, and the transceiver may be further configured to receive one or more reference measurements. Building the calibration buffer may include, for each of the one or more reference measurements, measuring an ADC Sig On level for the gain of the amplifier before changing to the calculated new gain and for the calculated new gain, and the calibration buffer may include the one or more reference measurements and the measured ADC Sig On levels.

Another aspect of the invention may provide a method including using a detector of an analyte sensor to detect one or more detectable properties exhibited by an indicator of the analyte sensor based on an amount or concentration of an analyte in proximity to the indicator. The method may include using an amplifier of the analyte sensor to amplify the analyte signal. The method may include using a transceiver to adjust a gain of the amplifier.

In some embodiments, the method may further include using an analog-to-digital converter (ADC) to quantize the amplified analyte signal. In some embodiments, adjusting the gain of the amplifier may include increasing the gain of the amplifier. In some of the embodiments, the method may further include using the transceiver to adjust a drive current of a light source of the analyte sensor.

In some embodiments, the method may include using the transceiver to determine whether one or more initial conditions are met. In some embodiments, determining whether the one or more initial conditions are met may include calculating a responsivity and determining whether the calculated responsivity is below a responsivity threshold. In some embodiments, the responsivity may be the responsiveness of the indicator of the analyte sensor to changes in the amount or concentration of the analyte in proximity to the indicator. In some embodiments, determining whether the one or more initial conditions are met may further include determining one or more of (i) whether a first threshold amount of time has passed since implantation or insertion of the analyte sensor, (ii) whether a second threshold amount of time has passed since a previous adjustment of the gain of the amplifier, and (iii) whether the gain of the amplifier has not been adjusted since the analyte sensor was implanted or inserted. In some embodiments, the transceiver may determine that the one or more initial conditions are met if the transceiver determines that (1) the first threshold amount of time has passed since implantation or insertion of the analyte sensor, (2) the gain of the amplifier has not been adjusted since the analyte sensor was implanted or inserted or the second threshold amount of time has passed since the previous adjustment of the gain of the amplifier, and (3) the calculated responsivity is below the responsivity threshold. In some embodiments, the method may further include using the transceiver to, if the transceiver determines that the one or more initial conditions are met, determine whether one or more pre-converge conditions are met.

In some embodiments, the method may include using the transceiver to determine whether one or more pre-converge conditions are met. In some embodiments, determining whether the one or more pre-converge conditions are met may include determining one or more of (i) whether a level of a battery of the transceiver is above a battery threshold, (ii) whether a rate of change of the amount or concentration of the analyte in proximity to the indicator is below an analyte rate of change threshold, (iii) whether the amount or concentration of the analyte in proximity to the indicator is within an analyte level range, (iv) whether a rate of change of a temperature of the analyte sensor is below a temperature rate of change threshold, (v) whether the temperature of the analyte sensor is within a temperature range, (vi) whether a time of the transceiver is within a time range, (vii) whether there were any ambient light alarms during the past hour, and (viii) whether there are any active ambient light alarms. In some embodiments, the transceiver may determine that the one or more pre-converge conditions are met if the transceiver determines that (i) the level of the battery of the transceiver is above the battery threshold, (ii) the rate of change of the amount or concentration of the analyte in proximity to the indicator is below the analyte rate of change threshold, (iii) the amount or concentration of the analyte in proximity to the indicator is within the analyte level range, (iv) the rate of change of the temperature of the analyte sensor is below the temperature rate of change threshold, (v) the temperature of the analyte sensor is within the temperature range, (vi) the time of the transceiver is within the time range, (vii) there were no ambient light alarms during the past hour, and (viii) there are no active ambient light alarms. In some embodiments, the method may further include using the transceiver to adjust the gain of the amplifier only if the transceiver determines that the one or more pre-converge conditions are met.

In some embodiments, adjusting the gain of the amplifier may include calculating a new gain for the amplifier of the analyte sensor and changing the gain of the amplifier to the calculated new gain. In some embodiments, adjusting the gain of the amplifier may further include building a calibration buffer. In some embodiments, the method may further include using an analog-to-digital converter (ADC) of the analyte sensor to quantize the amplified analyte signal and using the transceiver to receive one or more reference measurements. In some embodiments, building the calibration buffer may include, for each of the one or more reference measurements, measuring an ADC Sig On level for the gain of the amplifier before changing to the calculated new gain and for the calculated new gain, and the calibration buffer may include the one or more reference measurements and the measured ADC Sig On levels.

Still another aspect of the invention may provide an analyte monitoring system including an analyte sensor and a transceiver. The analyte sensor may include an indicator, a light source, and a detector. The indicator may be configured to exhibit one or more detectable properties based on an amount or concentration of an analyte in proximity to the indicator. The light source may be configured to irradiate the indicator with excitation light. The detector may be configured to detect one or more of the detectable properties and output an analyte signal indicative of the amount or concentration of the analyte in proximity to the indicator. The transceiver may be configured to adjust a drive current of the light source.

Yet another aspect of the invention may provide a method including using a light source of an analyte sensor to irradiate an indicator of the analyte sensor with excitation light. The method may include using a detector of the analyte sensor to detect one or more detectable properties exhibited by the indicator of the analyte sensor based on an amount or concentration of an analyte in proximity to the indicator. The method may include using a transceiver to adjust a drive current of a light source of the analyte sensor.

Further variations encompassed within the systems and methods are described in the detailed description of the invention below.

BRIEF DESCRIPTION OF THE DRAWINGS

The accompanying drawings, which are incorporated herein and form part of the specification, illustrate various, non-limiting embodiments of the present invention. In the drawings, like reference numbers indicate identical or functionally similar elements.

DETAILED DESCRIPTION OF PREFERRED EMBODIMENTS

Figure 1:
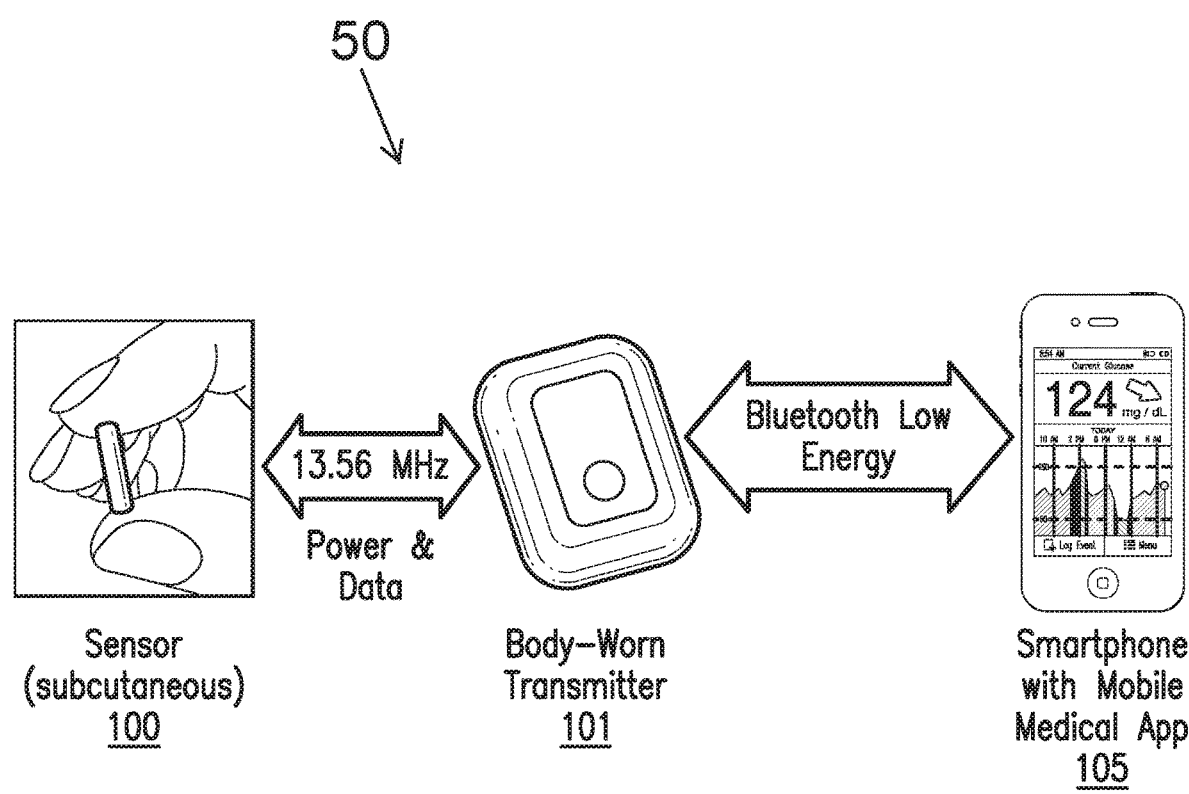
FIG. 1 is a schematic view illustrating an analyte monitoring system embodying aspects of the present invention.

FIG. 1 is a schematic view of an exemplary analyte monitoring system 50 embodying aspects of the present invention. The analyte monitoring system 50 may be a continuous analyte monitoring system (e.g., a continuous glucose monitoring system). In some embodiments, the analyte monitoring system 50 may include one or more of an analyte sensor 100, a transceiver 101, and a display device 105. In some embodiments, the sensor 100 may be small, fully subcutaneously implantable sensor measures analyte (e.g., glucose) concentrations in a medium (e.g., interstitial fluid) of a living animal (e.g., a living human). However, this is not required, and, in some alternative embodiments, the sensor 100 may be a partially implantable (e.g., transcutaneous) sensor or a fully external sensor. In some embodiments, the transceiver 101 may be an externally worn transceiver (e.g., attached via an armband, wristband, waistband, or adhesive patch). In some embodiments, the transceiver 101 may remotely power and/or communicate with the sensor to initiate and receive the measurements (e.g., via near field communication (NFC)). However, this is not required, and, in some alternative embodiments, the transceiver 101 may power and/or communicate with the sensor 100 via one or more wired connections. In some non-limiting embodiments, the transceiver 101 may be a smartphone (e.g., an NFC-enabled smartphone). In some embodiments, the transceiver 101 may communicate information (e.g., one or more analyte concentrations) wirelessly (e.g., via a Bluetooth™ communication standard such as, for example and without limitation Bluetooth Low Energy) to a hand held application running on a display device 105 (e.g., smartphone). In some embodiments, information can be downloaded from the transceiver 101 through a Universal Serial Bus (USB) port. In some embodiments, the analyte monitoring system 50 may include a web interface for plotting and sharing of uploaded data.

Figure 2:
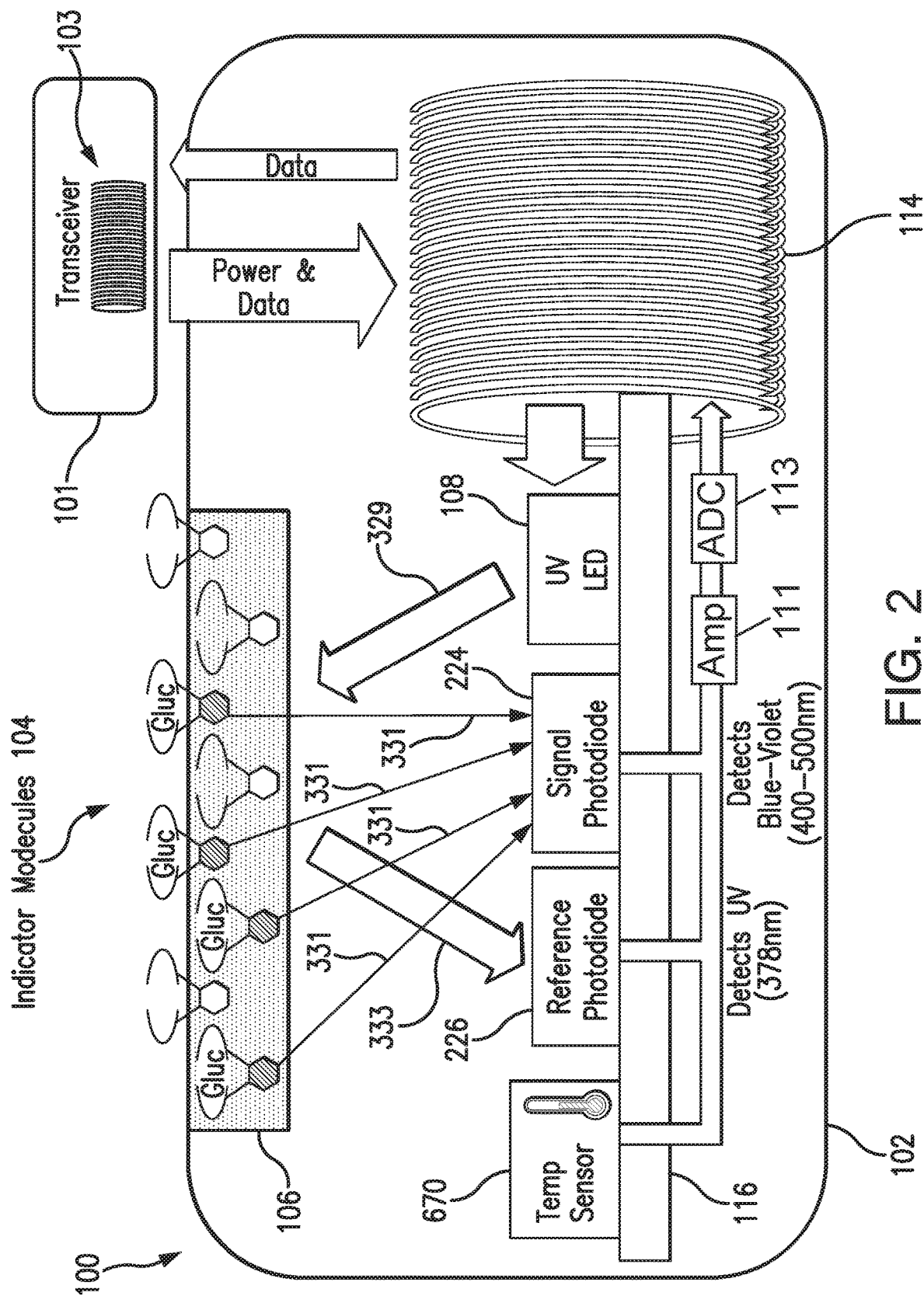
FIG. 2 is a schematic view illustrating a sensor and transceiver of an analyte monitoring system embodying aspects of the present invention.

In some embodiments, as illustrated in FIG. 2, the transceiver 101 may include an inductive element 103, such as, for example, a coil. The transceiver 101 may generate an electromagnetic wave or electrodynamic field (e.g., by using a coil) to induce a current in an inductive element 114 of the sensor 100, which powers the sensor 100. The transceiver 101 may also convey data (e.g., commands) to the sensor 100. For example, in a non-limiting embodiment, the transceiver 101 may convey data by modulating the electromagnetic wave used to power the sensor 100 (e.g., by modulating the current flowing through a coil 103 of the transceiver 101). The modulation in the electromagnetic wave generated by the transceiver 101 may be detected/extracted by the sensor 100. Moreover, the transceiver 101 may receive data (e.g., measurement information) from the sensor 100. For example, in a non-limiting embodiment, the transceiver 101 may receive data by detecting modulations in the electromagnetic wave generated by the sensor 100, e.g., by detecting modulations in the current flowing through the coil 103 of the transceiver 101.

The inductive element 103 of the transceiver 101 and the inductive element 114 of the sensor 100 may be in any configuration that permits adequate field strength to be achieved when the two inductive elements are brought within adequate physical proximity.

In some non-limiting embodiments, as illustrated in FIG. 2, the sensor 100 may be encased in a sensor housing 102 (i.e., body, shell, capsule, or encasement), which may be rigid and biocompatible. The sensor 100 may include an analyte indicator 106, such as, for example, a polymer graft coated, diffused, adhered, or embedded on or in at least a portion of the exterior surface of the sensor housing 102. The analyte indicator 106 (e.g., polymer graft) of the sensor 100 may include indicator molecules 104 (e.g., fluorescent indicator molecules) exhibiting one or more detectable properties (e.g., optical properties) based on the amount or concentration of the analyte in proximity to the analyte indicator 106. In some embodiments, the sensor 100 may include a light source 108 that emits excitation light 329 over a range of wavelengths that interact with the indicator molecules 104. The sensor 100 may also include one or more photodetectors 224, 226 (e.g., photodiodes, phototransistors, photoresistors, or other photosensitive elements). The one or more photodetectors (e.g., photodetector 224) may be sensitive to emission light 331 (e.g., fluorescent light) emitted by the indicator molecules 104 such that a signal generated by a photodetector (e.g., photodetector 224) in response thereto that is indicative of the level of emission light 331 of the indicator molecules and, thus, the amount of analyte of interest (e.g., glucose). In some non-limiting embodiments, one or more of the photodetectors (e.g., photodetector 226) may be sensitive to excitation light 329 that is reflected from the analyte indicator 106 as reflection light 333. In some non-limiting embodiments, one or more of the photodetectors may be covered by one or more filters (e.g., bandpass filter 112 of FIG. 6) that allow only a certain subset of wavelengths of light to pass through (e.g., a subset of wavelengths corresponding to emission light 331 or a subset of wavelengths corresponding to reflection light 333) and reflect the remaining wavelengths. In some non-limiting embodiments, the sensor 100 may include a temperature transducer 670. In some non-limiting embodiments, the sensor 100 may include a drug-eluting polymer matrix that disperses one or more therapeutic agents (e.g., an anti-inflammatory drug).

In some embodiments, the outputs of one or more of the photodetectors 224, 226 and the temperature transducer 670 may be amplified by an amplifier 111. In some non-limiting embodiments, the amplifier 111 may be a comparator that receives analog light measurement signals from the photodetectors 224, 226 and output an analog light difference measurement signal indicative of the difference between the received analog light measurement signals. In some non-limiting embodiments, the amplifier 111 may be a transimpedance amplifier. However, in some alternative embodiments, a different amplifier may be used. In some embodiments, the outputs of one or more of the photodetectors 224, 226, the temperature transducer 670, and the amplifier 111 may be converted to a digital signal by an analog-to-digital converter (ADC) 113.

In some embodiments, one or more of the gain of the amplifier 111 and the drive current of the light source 108 may be initially set during a quality control process. In some embodiments, one or more of the gain of the amplifier 111 and the drive current of the light source 108 may be set to allow high dynamic range and to keep the modulated signal within the operational region. In some embodiments, any change (e.g., increase or decrease) to one or more of the drive current of the light source 108 and the gain of the amplifier 111 may change the modulated signal level accordingly.

In some embodiments, as illustrated in FIG. 2, the sensor 100 may include a substrate 116. In some embodiments, the substrate 116 may be a circuit board (e.g., a printed circuit board (PCB) or flexible PCB) on which circuit components (e.g., analog and/or digital circuit components) may be mounted or otherwise attached. However, in some alternative embodiments, the substrate 116 may be a semiconductor substrate having circuitry fabricated therein. The circuitry may include analog and/or digital circuitry. Also, in some semiconductor substrate embodiments, in addition to the circuitry fabricated in the semiconductor substrate, circuitry may be mounted or otherwise attached to the semiconductor substrate 116. In other words, in some semiconductor substrate embodiments, a portion or all of the circuitry, which may include discrete circuit elements, an integrated circuit (e.g., an application specific integrated circuit (ASIC)) and/or other electronic components (e.g., a non-volatile memory), may be fabricated in the semiconductor substrate 116 with the remainder of the circuitry is secured to the semiconductor substrate 116 and/or a core (e.g., ferrite core) for the inductive element 114. In some embodiments, the semiconductor substrate 116 and/or a core may provide communication paths between the various secured components.

In some embodiments, the one or more of the sensor housing 102, analyte indicator 106, indicator molecules 104, light source 108, photodetectors 224, 226, temperature transducer 670, substrate 116, and inductive element 114 of sensor 100 may include some or all of the features described in one or more of U.S. application Ser. No. 13/761,839, filed on Feb. 7, 2013, U.S. application Ser. No. 13/937,871, filed on Jul. 9, 2013, and U.S. application Ser. No. 13/650,016, filed on Oct. 11, 2012, all of which are incorporated by reference in their entireties. Similarly, the structure and/or function of the sensor 100 and/or transceiver 101 may be as described in one or more of U.S. application Ser. Nos. 13/761,839, 13/937,871, and 13/650,016.

Although in some embodiments, as illustrated in FIG. 2, the sensor 100 may be an optical sensor, this is not required, and, in one or more alternative embodiments, sensor 100 may be a different type of analyte sensor, such as, for example, an electrochemical sensor, a diffusion sensor, or a pressure sensor. Also, although in some embodiments, as illustrated in FIGS. 1 and 2, the analyte sensor 100 may be a fully implantable sensor, this is not required, and, in some alternative embodiments, the sensor 100 may be a transcutaneous sensor having a wired connection to the transceiver 101. For example, in some alternative embodiments, the sensor 100 may be located in or on a transcutaneous needle (e.g., at the tip thereof). In these embodiments, instead of wirelessly communicating using inductive elements 103 and 114, the sensor 100 and transceiver 101 may communicate using one or more wires connected between the transceiver 101 and the transceiver transcutaneous needle that includes the sensor 100. For another example, in some alternative embodiments, the sensor 100 may be located in a catheter (e.g., for intravenous blood glucose monitoring) and may communicate (wirelessly or using wires) with the transceiver 101.

In some embodiments, the sensor 100 may include a transceiver interface device. In some embodiments where the sensor 100 includes an antenna (e.g., inductive element 114), the transceiver interface device may include the antenna (e.g., inductive element 114) of sensor 100. In some of the transcutaneous embodiments where there exists a wired connection between the sensor 100 and the transceiver 101, the transceiver interface device may include the wired connection.

Figure 3:
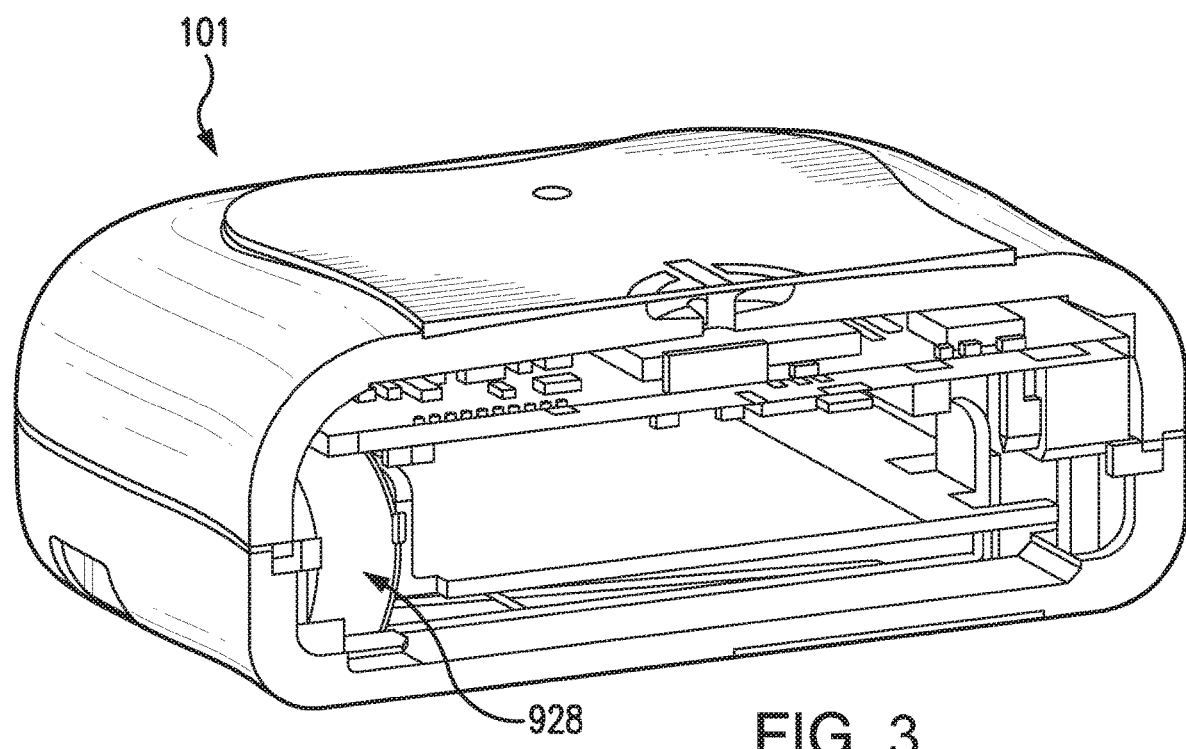
FIG. 3 is cross-sectional, perspective view of a transceiver embodying aspects of the invention.
Figure 4:
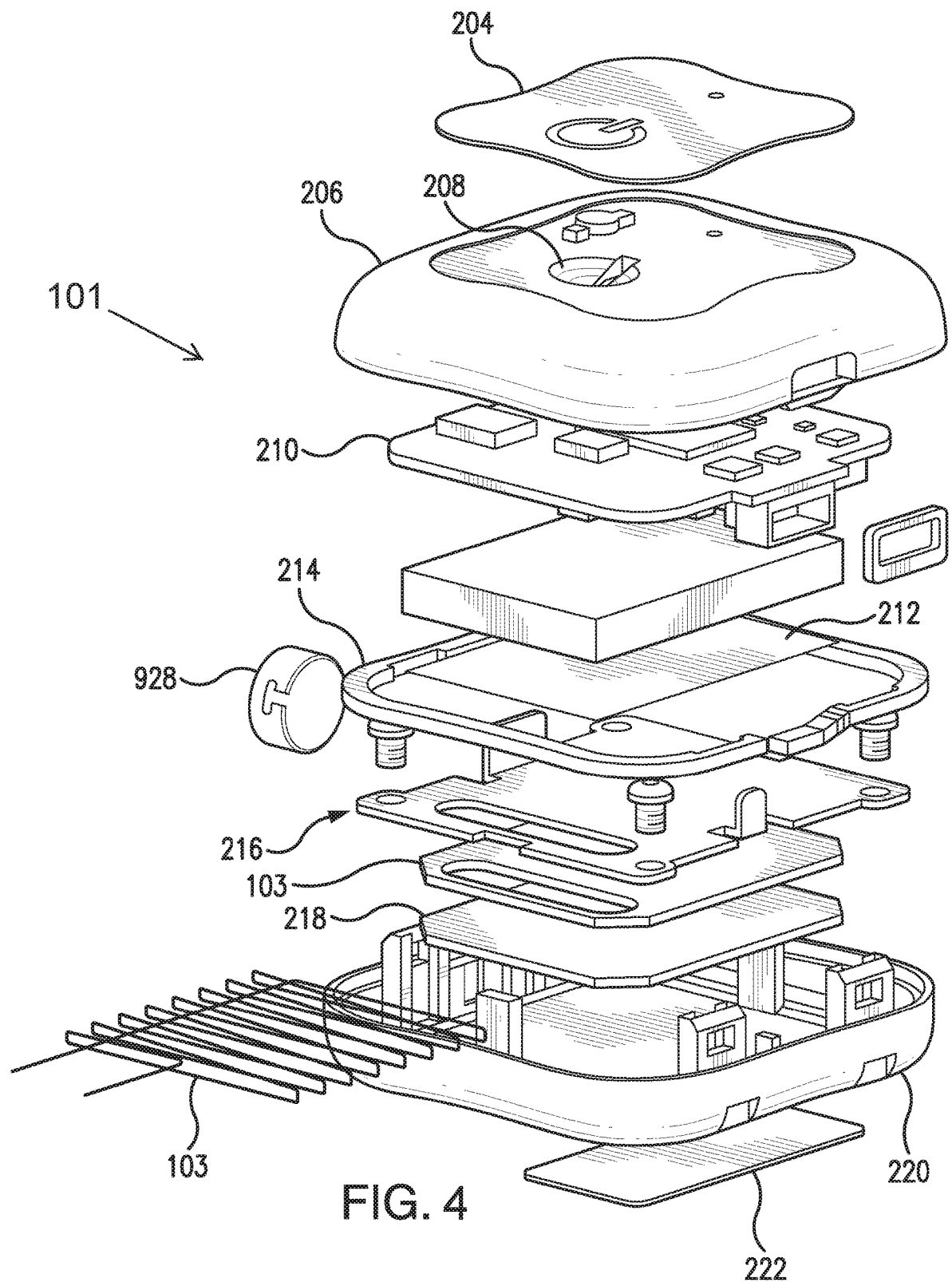
FIG. 4 is an exploded, perspective view of a transceiver embodying aspects of the invention.

FIGS. 3 and 4 are cross-sectional and exploded views, respectively, of a non-limiting embodiment of the transceiver 101, which may be included in the analyte monitoring system illustrated in FIG. 1. As illustrated in FIG. 4, in some non-limiting embodiments, the transceiver 101 may include a graphic overlay 204, front housing 206, button 208, printed circuit board (PCB) assembly 210, battery 212, gaskets 214, antenna 103, frame 218, reflection plate 216, back housing 220, ID label 222, and/or vibration motor 928. In some non-limiting embodiments, the vibration motor 928 may be attached to the front housing 206 or back housing 220 such that the battery 212 does not dampen the vibration of vibration motor 928. In a non-limiting embodiment, the transceiver electronics may be assembled using standard surface mount device (SMD) reflow and solder techniques. In one embodiment, the electronics and peripherals may be put into a snap together housing design in which the front housing 206 and back housing 220 may be snapped together. In some embodiments, the full assembly process may be performed at a single external electronics house. However, this is not required, and, in alternative embodiments, the transceiver assembly process may be performed at one or more electronics houses, which may be internal, external, or a combination thereof. In some embodiments, the assembled transceiver 101 may be programmed and functionally tested. In some embodiments, assembled transceivers 101 may be packaged into their final shipping containers and be ready for sale.

In some embodiments, as illustrated in FIGS. 3 and 4, the antenna 103 may be contained within the housing 206 and 220 of the transceiver 101. In some embodiments, the antenna 103 in the transceiver 101 may be small and/or flat so that the antenna 103 fits within the housing 206 and 220 of a small, lightweight transceiver 101. In some embodiments, the antenna 103 may be robust and capable of resisting various impacts. In some embodiments, the transceiver 101 may be suitable for placement, for example, on an abdomen area, upper-arm, wrist, or thigh of a patient body. In some non-limiting embodiments, the transceiver 101 may be suitable for attachment to a patient body by means of a biocompatible patch. Although, in some embodiments, the antenna 103 may be contained within the housing 206 and 220 of the transceiver 101, this is not required, and, in some alternative embodiments, a portion or all of the antenna 103 may be located external to the transceiver housing. For example, in some alternative embodiments, antenna 103 may wrap around a user's wrist, arm, leg, or waist such as, for example, the antenna described in U.S. Pat. No. 8,073,548, which is incorporated herein by reference in its entirety.

Figure 5:
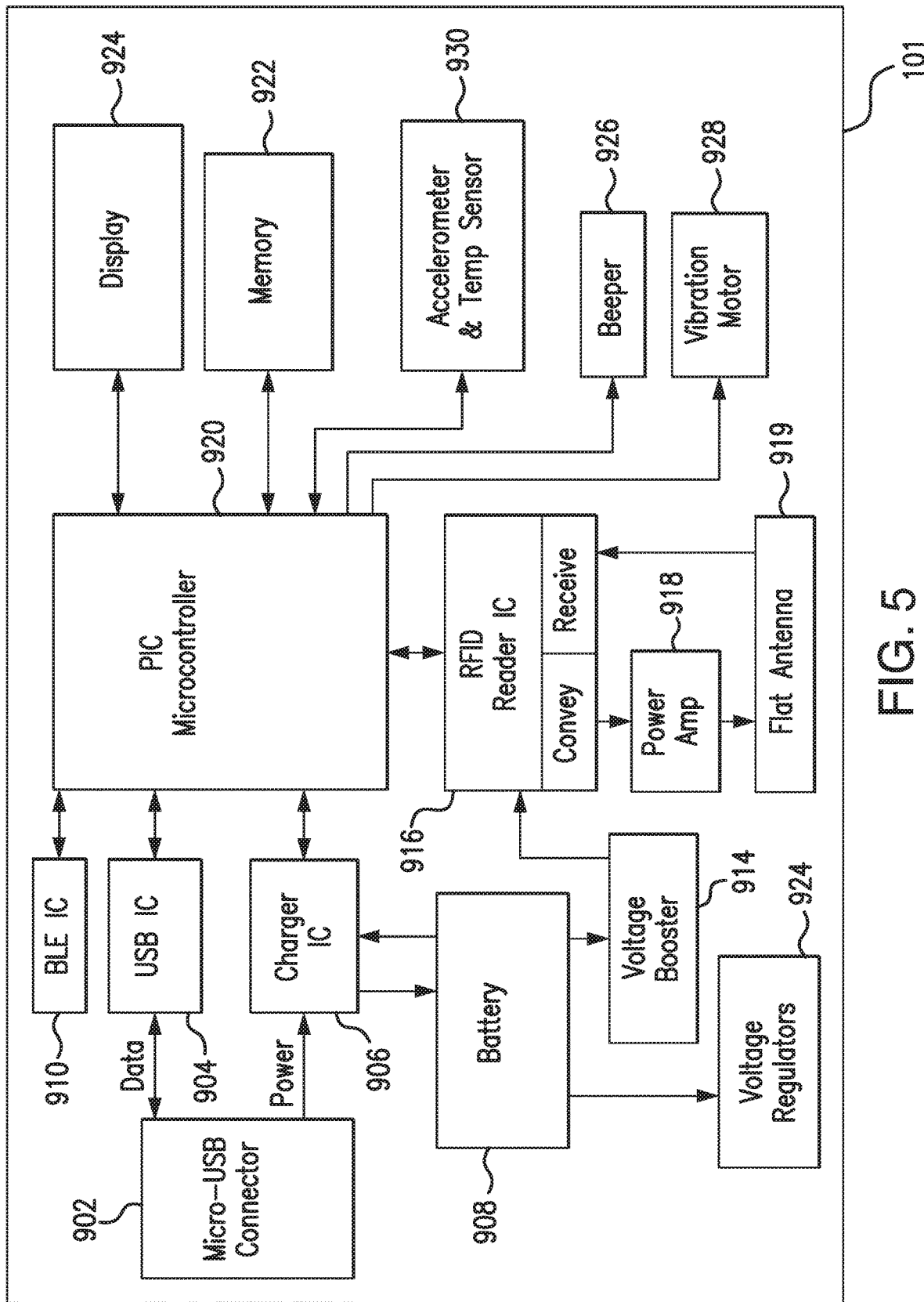
FIG. 5 is a schematic view illustrating a transceiver embodying aspects of the present invention.

FIG. 5 is a schematic view of an external transceiver 101 according to a non-limiting embodiment. In some embodiments, the transceiver 101 may have a connector 902, such as, for example, a Micro-Universal Serial Bus (USB) connector. The connector 902 may enable a wired connection to an external device, such as a personal computer (e.g., personal computer 109) or a display device 105 (e.g., a smartphone).

The transceiver 101 may exchange data to and from the external device through the connector 902 and/or may receive power through the connector 902. The transceiver 101 may include a connector integrated circuit (IC) 904, such as, for example, a USB-IC, which may control transmission and receipt of data through the connector 902. The transceiver 101 may also include a charger IC 906, which may receive power via the connector 902 and charge a battery 908 (e.g., lithium-polymer battery). In some embodiments, the battery 908 may be rechargeable, may have a short recharge duration, and/or may have a small size.

In some embodiments, the transceiver 101 may include one or more connectors in addition to (or as an alternative to) Micro-USB connector 904. For example, in one alternative embodiment, the transceiver 101 may include a spring-based connector (e.g., Pogo pin connector) in addition to (or as an alternative to) Micro-USB connector 904, and the transceiver 101 may use a connection established via the spring-based connector for wired communication to a personal computer (e.g., personal computer 109) or a display device 105 (e.g., a smartphone) and/or to receive power, which may be used, for example, to charge the battery 908.

In some embodiments, the transceiver 101 may have a wireless communication IC 910, which enables wireless communication with an external device, such as, for example, one or more personal computers (e.g., personal computer 109) or one or more display devices 105 (e.g., a smartphone). In one non-limiting embodiment, the wireless communication IC 910 may employ one or more wireless communication standards to wirelessly transmit data. The wireless communication standard employed may be any suitable wireless communication standard, such as an ANT standard, a Bluetooth standard, or a Bluetooth Low Energy (BLE) standard (e.g., BLE 4.0). In some non-limiting embodiments, the wireless communication IC 910 may be configured to wirelessly transmit data at a frequency greater than 1 gigahertz (e.g., 2.4 or 5 GHz). In some embodiments, the wireless communication IC 910 may include an antenna (e.g., a Bluetooth antenna). In some non-limiting embodiments, the antenna of the wireless communication IC 910 may be entirely contained within the housing (e.g., housing 206 and 220) of the transceiver 101. However, this is not required, and, in alternative embodiments, all or a portion of the antenna of the wireless communication IC 910 may be external to the transceiver housing.

In some embodiments, the transceiver 101 may include a display interface device, which may enable communication by the transceiver 101 with one or more display devices 105. In some embodiments, the display interface device may include the antenna of the wireless communication IC 910 and/or the connector 902. In some non-limiting embodiments, the display interface device may additionally include the wireless communication IC 910 and/or the connector IC 904.

In some embodiments, the transceiver 101 may include voltage regulators 912 and/or a voltage booster 914. The battery 908 may supply power (via voltage booster 914) to radio-frequency identification (RFID) reader IC 916, which uses the inductive element 103 to convey information (e.g., commands) to the sensor 101 and receive information (e.g., measurement information) from the sensor 100. In some non-limiting embodiments, the sensor 100 and transceiver 101 may communicate using near field communication (NFC) (e.g., at a frequency of 13.56 MHz). In the illustrated embodiment, the inductive element 103 is a flat antenna. In some non-limiting embodiments, the antenna may be flexible. However, as noted above, the inductive element 103 of the transceiver 101 may be in any configuration that permits adequate field strength to be achieved when brought within adequate physical proximity to the inductive element 114 of the sensor 100. In some embodiments, the transceiver 101 may include a power amplifier 918 to amplify the signal to be conveyed by the inductive element 103 to the sensor 100.

The transceiver 101 may include a peripheral interface controller (PIC) microcontroller 920 and memory 922 (e.g., Flash memory), which may be non-volatile and/or capable of being electronically erased and/or rewritten. The PIC microcontroller 920 may control the overall operation of the transceiver 101. For example, the PIC microcontroller 920 may control the connector IC 904 or wireless communication IC 910 to transmit data via wired or wireless communication and/or control the RFID reader IC 916 to convey data via the inductive element 103. The PIC microcontroller 920 may also control processing of data received via the inductive element 103, connector 902, or wireless communication IC 910.

In some embodiments, the transceiver 101 may include a sensor interface device, which may enable communication by the transceiver 101 with a sensor 100. In some embodiments, the sensor interface device may include the inductive element 103. In some non-limiting embodiments, the sensor interface device may additionally include the RFID reader IC 916 and/or the power amplifier 918. However, in some alternative embodiments where there exists a wired connection between the sensor 100 and the transceiver 101 (e.g., transcutaneous embodiments), the sensor interface device may include the wired connection.

In some embodiments, the transceiver 101 may include a display 924 (e.g., liquid crystal display and/or one or more light emitting diodes), which PIC microcontroller 920 may control to display data (e.g., analyte concentration values). In some embodiments, the transceiver 101 may include a speaker 926 (e.g., a beeper) and/or vibration motor 928, which may be activated, for example, in the event that an alarm condition (e.g., detection of a hypoglycemic or hyperglycemic condition) is met. The transceiver 101 may also include one or more additional sensors 930, which may include an accelerometer and/or temperature sensor, that may be used in the processing performed by the PIC microcontroller 920.

In some embodiments, the transceiver 101 may be a body-worn transceiver that is a rechargeable, external device worn over the sensor implantation or insertion site. The transceiver 101 may supply power to the proximate sensor 100, calculate analyte concentrations from data received from the sensor 100, and/or transmit the calculated analyte concentrations to a display device 105 (see FIG. 1). Power may be supplied to the sensor 100 through an inductive link (e.g., an inductive link of 13.56 MHz). In some embodiments, the transceiver 101 may be placed using an adhesive patch or a specially designed strap or belt. The external transceiver 101 may read measured analyte data from a subcutaneous sensor 100 (e.g., up to a depth of 2 cm or more). The transceiver 101 may periodically (e.g., every 2, 5, or 10 minutes) read sensor data and calculate an analyte concentration and an analyte concentration trend. From this information, the transceiver 101 may also determine if an alert and/or alarm condition exists, which may be signaled to the user (e.g., through vibration by vibration motor 928 and/or an LED of the transceiver's display 924 and/or a display of a display device 105). The information from the transceiver 101 (e.g., calculated analyte concentrations, calculated analyte concentration trends, alerts, alarms, and/or notifications) may be transmitted to a display device 105 (e.g., via Bluetooth Low Energy with Advanced Encryption Standard (AES)-Counter CBC-MAC (CCM) encryption) for display by a mobile medical application (MMA) being executed by the display device 105. In some non-limiting embodiments, the MMA may provide alarms, alerts, and/or notifications in addition to any alerts, alarms, and/or notifications received from the transceiver 101. In one embodiment, the MMA may be configured to provide push notifications. In some embodiments, the transceiver 101 may have a power button (e.g., button 208) to allow the user to turn the device on or off, reset the device, or check the remaining battery life. In some embodiments, the transceiver 101 may have a button, which may be the same button as a power button or an additional button, to suppress one or more user notification signals (e.g., vibration, visual, and/or audible) of the transceiver 101 generated by the transceiver 101 in response to detection of an alert or alarm condition.

In some embodiments, the transceiver 101 of the analyte monitoring system 50 receives raw signals indicative of an amount or concentration of an analyte in proximity to the analyte indicator 106 of the analyte sensor 100. In some embodiments, the transceiver 101 may receive the raw signals from the sensor 100 periodically (e.g., every 5, 10, or 20 minutes). In some embodiments, the raw signals may include one or more analyte measurements (e.g., one or more measurements indicative of the level of emission light 331 from the indicator molecules 104 as measured by the photodetector 224) and/or one or more temperature measurements (e.g., as measured by the temperature transducer 670). In some embodiments, the transceiver 101 may use the received raw signals to calculate analyte concentration. In some embodiments, the transceiver 100 may store one or more calculated analyte concentrations (e.g., in memory 922). In some embodiments, the transceiver 100 may convey one or more calculated analyte concentrations to the display device 105.

In some embodiments, the analyte monitoring system 50 may calibrate the conversion of raw signals to analyte concentration. In some embodiments, the calibration may be performed approximately periodically (e.g., every 12 or 24 hours). In some embodiments, the calibration may be performed using one or more reference measurements (e.g., one or more self-monitoring blood glucose (SMBG) measurements), which may be entered into the analyte monitoring system 50 using the user interface of the display device 105. In some embodiments, the transceiver 101 may receive the one or more reference measurements from the display device 105 and perform the calibration.

Figure 6:
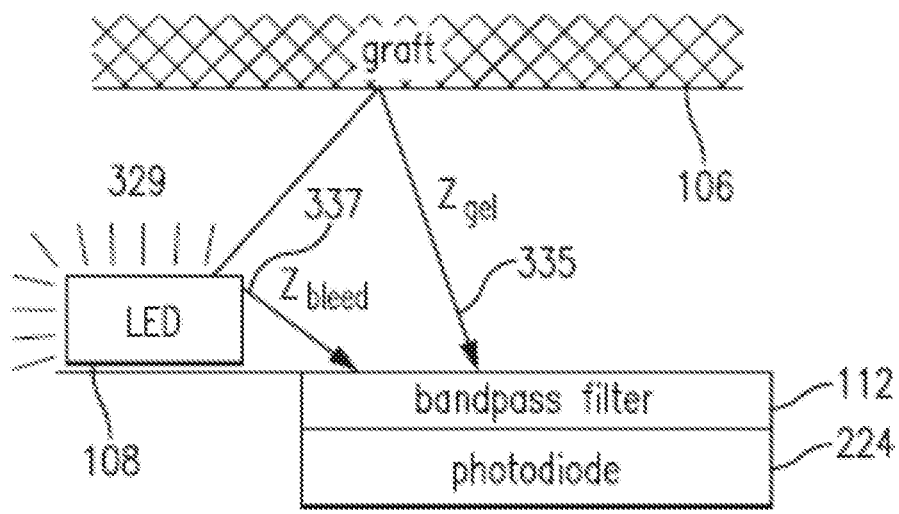
FIG. 6 illustrates the components of the excitation light received by the photodetector that contribute to the offset in the raw signal in accordance with an embodiment of the present invention.

FIG. 6 illustrates the Zgel (i.e., opacity) and Zbleed offset components that may be in the light that reaches a photodetector of the sensor 100. As illustrated in FIG. 6, the excitation light 329 emitted from light source 108 that reaches the photodetector may include (i) a reflection light component 335 that is reflected from the analyte indicator 106 (e.g., indicator molecules 104 in a gel) before reaching the photodetector and (ii) a bleed light component 337 that reaches the photodetector without encountering the analyte indicator 106. The reflection light component 335 may produce a reflection component $Z_{gel}$ of the offset, and the bleed light component 337 may produce a bleed component $Z_{bleed}$ of the offset Z.

In some embodiments, after implantation or implantation of the sensor 100, the sensor 100 may begin to experience modulation loss (e.g., a decrease in the change in the amount of emission light 331 emitted by the indicator molecules 104 of the indicator 106 as the amount of analyte in the presence of the indicator molecules 104 changes) over time. In some non-limiting embodiments, the modulation loss may be, for example and without limitation, due to oxidative de-boronation of the indicator 106, which may be induced by the body's immune system.

In some embodiments, the analyte modulated signal (e.g., the output of the signal photodetector 224, which may be indicative of the amount of emission light 331 emitted by the indicator molecules 104 of the indicator 106), which may be amplified by the amplifier 111, is sampled using the ADC 113 and then represented by ADC bits, also known as counts.

In some embodiments, the quantization level may be a linear representation of an interstitial fluid (ISF) analyte (e.g., glucose) level in ADC bits. In some non-limiting embodiments, high ISF analyte levels may be represented by higher ADC counts than lower ISF analyte levels. In some non-limiting embodiments:

$$\text{Quantization level } b = \frac{fmax - fmin}{2^n - 1} = \frac{GlucoseMax - GlucoseMin}{2^{ADC\ Bits\ used} - 1}$$

where fmax is the highest ISF analyte level number, fmin is the lowest ISF analyte level, and n is the number of ADC bits used to represent the sampled values. In one non-limiting embodiment, fmax may be, for example and without limitation, 400 [mgdL], fmin may be, for example and without limitation, 40 [mgdL], and n may be, for example and without limitation, 11 bits. In this non-limiting example, the quantization level may be as shown below:

$$\text{Quantization level} =$$
$$\frac{GlucoseMax - GlucoseMin}{2^{ADC\ Bits\ used} - 1} = \frac{400 - 40}{2^{11} - 1} = \frac{360}{2047} = 0.1759 \text{ [mg/dL]}$$

Thus, in this non-limiting example, each decrease or increase of 0.1759 [mg/dL] in the ISF analyte level may change the ADC count by 1, respectively.

Figure 7:
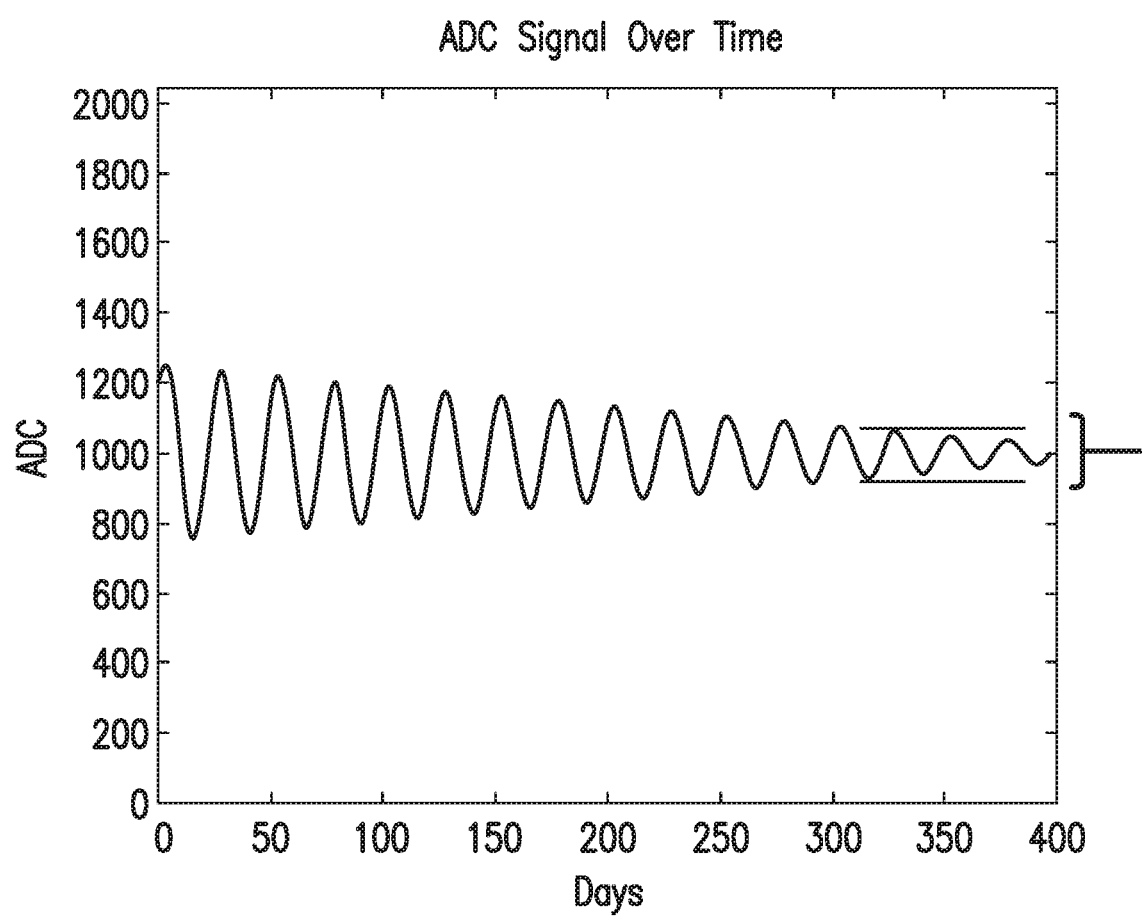
FIG. 7 illustrates a plot showing a non-limiting example of changes to the analog-to-digital converter (ADC) signal over time according to some embodiments.

In some non-limiting embodiments, not all of the ADC bits may be used to represent the ISF analyte level. For example, in a non-limiting embodiment having 11 ADC bits, fewer than all of the 11 ADC bits may be used to represented the ISF analyte level. In some embodiments, the baseline signal, which may comprise of $Z_{Bleed}$, $Z_{Gel}$ and other variables (see FIG. 6), may cause the modulated signal to have relatively high baseline values. In some non-limiting embodiments, the high baselines values may account for 50% of the total signal. Thus, in some embodiments, the number of ADC counts used to account for actual ISF analyte level change may become much smaller over time. For example and without limitation, the number of ADC counts used to account for actual ISF analyte level change may be estimated to be a total of 450 ADC counts at day 1 and 100-80 ADC counts after some time (e.g., after some degradation or at the end of senor life). In some non-limiting embodiments, the analyte monitoring system 50 may require a threshold number of ADC counts (e.g., 80-100 ADC counts) to maintain its accurate analyte sensing properties. FIG. 7 is a plot illustrating a non-limiting example of changes to the ADC signal over time in some embodiments of the present invention.

In some embodiments, the effective quantization level at the end of the life of a sensor 100 may be calculated using the following formula:

$$b = \frac{fmax - fmin}{2^{log_2(number\ of\ ADC\ counts\ used)} - 1} = \frac{400 - 40}{80 - 1} = \frac{360}{79} = 4.56 \text{ [mg/dL]}$$

where each 4.56 [mg/dL] ISF analyte change may results in 1 ADC count.

In some embodiments, the analyte monitoring system 50 may lower the quantization level by increasing one or more of the gain of the amplifier 111 and the drive current of the light source 108. In some embodiments, as shown by the equation below, while the remaining modulation may be a parameter controlled by the chemistry (e.g., gel chemistry) of the indicator 106, the analyte monitoring system 50 may control and update one or more of the gain of the amplifier 111 and the drive current of the light source 108. In some non-limiting embodiments, the analyte monitoring system 50 may control and update one or more of the gain of the amplifier 111 and the drive current of the light source 108 to compensate for the chemical modulation loss of the indicator 106. In some non-limiting embodiments, lowering the quantization level may be beneficial, and its mutual effect with the amplifier noise may be shown as:

$$\text{Quantization level} =$$
$$\frac{GlucoseMax - GlucoseMin}{2^{ADC\ Bits\ used} - 1} = \frac{fmax - fmin}{2^{log_2(modulation_{left} * LED_{current} * Gain)} - 1} =$$
$$\frac{fmax - fmin}{(modulation_{eft} * LED_{Current} * Gain) - 1} =$$
$$\frac{fmax - fmin}{(LED_{Current} * Gain) * (modulation_{eft}) - 1}$$

Figures 8, 9:
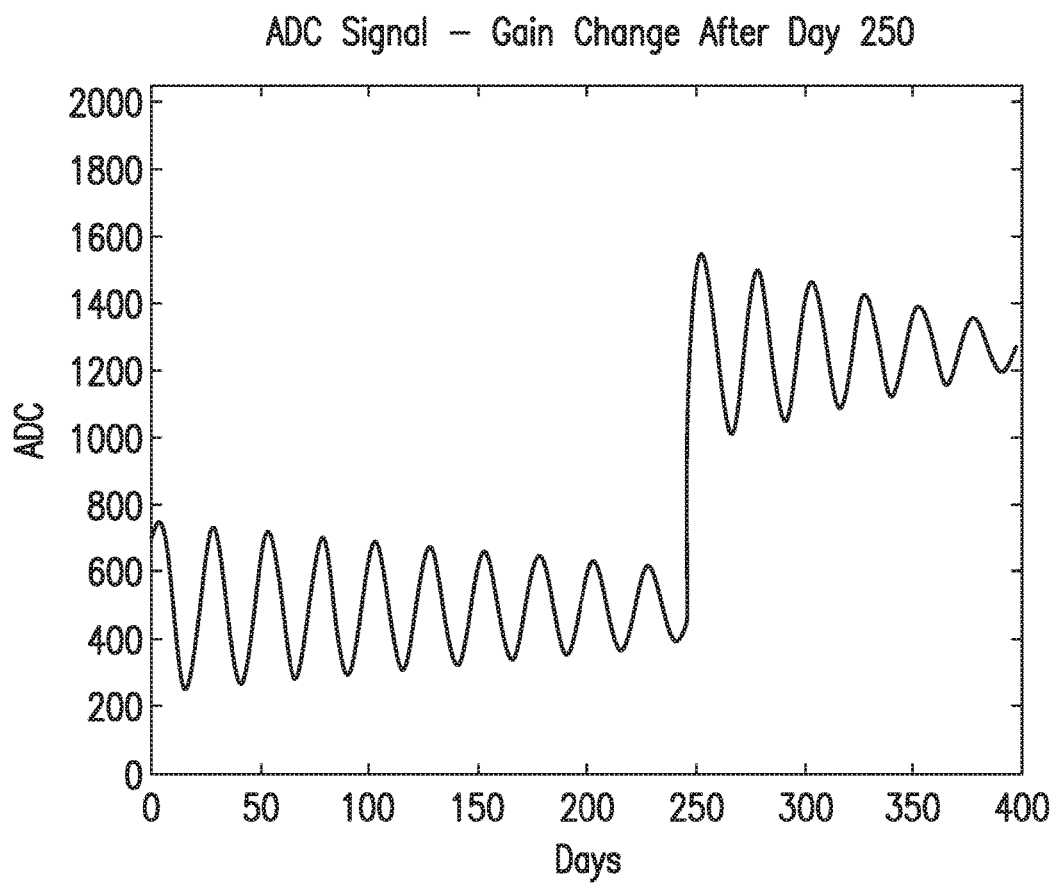
FIG. 8 illustrates a plot showing a non-limiting example of the effect that changing the amplifier gain may have on the ADC signal according to some embodiments.
FIG. 9 is a table showing glucose error as a factor of quantization levels, ADC noise, glucose levels, and amplifier Cal Gain in some non-limiting examples of the analyte monitoring system 50 according to some non-limiting embodiments.

FIG. 8 illustrates a plot showing a non-limiting example of the effect that changing the gain of the amplifier 111 after 250 days since implantation or insertion of the sensor 100 may have on the ADC signal output by the ADC 113.

In some embodiments, one might expect constant ADC readings in the presence of constant analyte levels. However, in some embodiments, small variations on the ADC reading may be present (e.g., due to one or more inherent noise sources). To evaluate the sensor's noise performance, in-vitro tests were done in a controlled environment, using constant analyte levels and ambient setting. FIG. 9 is a table showing glucose error as a factor of quantization levels, ADC noise, glucose levels, and amplifier Cal Gain in some non-limiting examples of the analyte monitoring system 50.

In some non-limiting embodiments, the indicator 106 may have a non-linear nature. In some non-limiting embodiments, due to the nonlinear nature of the analyte sensing indicator (Kd), the quantization level may be higher for higher glucose levels, which may worsen the mutual effect of the amplifier noise and the quantization levels.

In some embodiments, increasing one or more of the gain of the amplifier 111 and the drive current of the light source 108 may decrease the quantization level by a direct linear proportion, which in turn may decrease the glucose error caused by the ADC noise.

Figure 10:
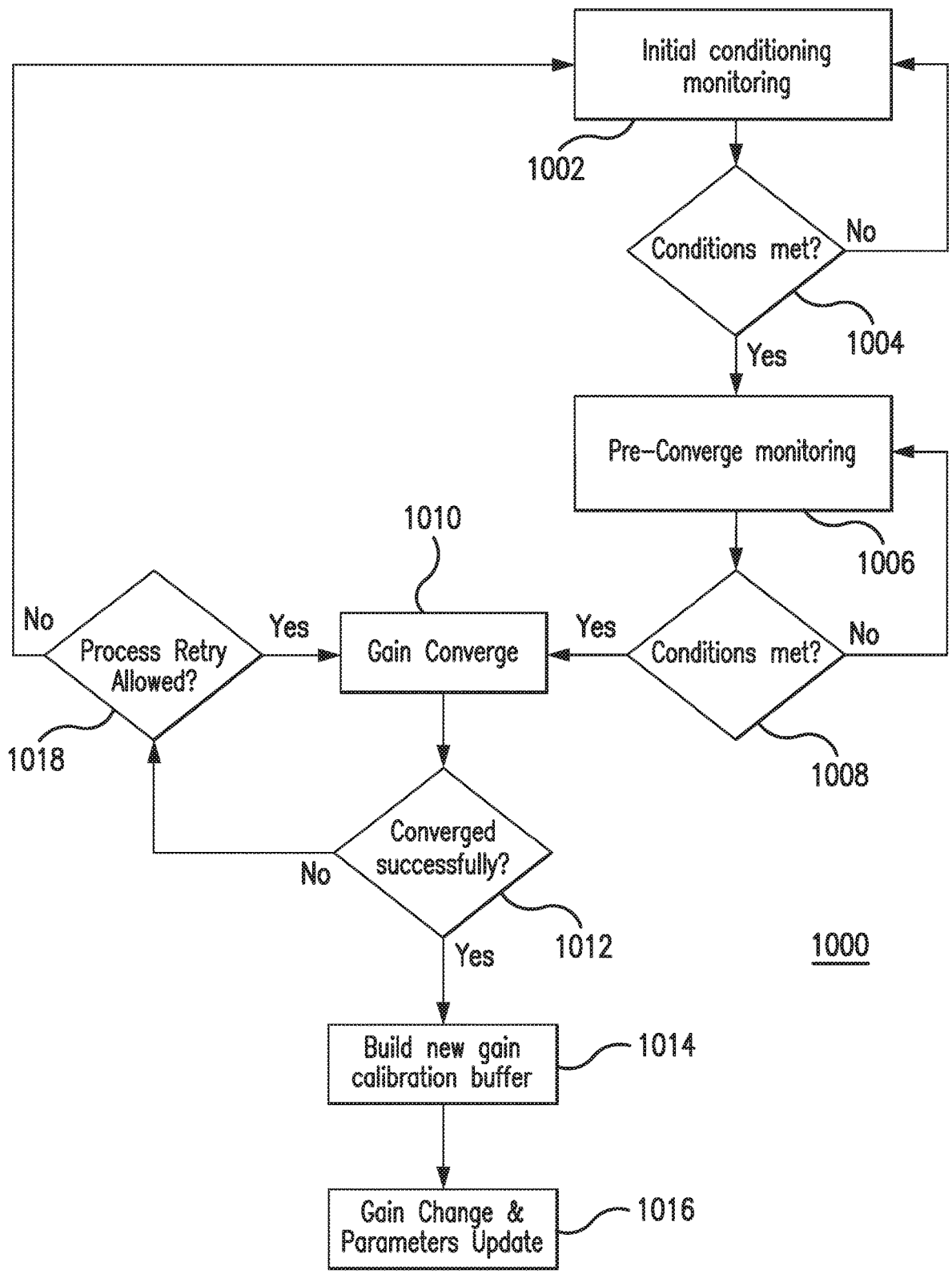
FIG. 10 is a flow chart illustrating a process for adjusting one or more parameters of the analyte monitoring system 50 embodying aspects of the present invention.

FIG. 10 is a flow chart illustrating a process 1000 for adjusting one or more parameters of the analyte monitoring system 50 according to some embodiments. In some embodiments, the transceiver 101 may perform one or more steps of the adjustment process 1000. In some embodiments, the PIC microcontroller 920 of the transceiver 101 may perform one or more steps of the adjustment process 1000. In some embodiments, prior to gain change, the adjustment process 1000 may monitor for appropriate signal levels and/or stability. In some embodiments, stable signals may enable accurate adjustment of the system parameters to the new gain. In some embodiments, adjusting one or more system parameters to a new gain may enable the analyte monitoring system 50 to continue display accurate analyte levels, without the need for an additional calibration point (e.g., self-monitoring blood glucose (SMBG) input).

In some embodiments, the adjustment process 1000 may autonomously decide whether to change one or more of a gain of the amplifier 111 and the drive current of the light source 108. In some embodiments, the adjustment process 110 may eliminate the need for one or more calibration points (e.g., SMBGs) from the user. In some embodiments, the adjustment process 1100 may not compromise the performance the performance of the analyte monitoring system 50. In some non-limiting embodiments, the analyte monitoring system 50 (e.g., the transceiver 101 of the system 50) may log any parameter changes (e.g., in the memory 922). In some embodiments, the adjustment process 1000 may minimize the risk of user disturbance.

In some embodiments, the adjustment process 1000 may include an initial condition monitoring step 1002 in which the transceiver 101 monitors one or more initial conditions. In some embodiments, the adjustment process 1000 may include a step 1104 in which the transceiver 101 determines whether one or more initial conditions are met. In some embodiments, if one or more of the initial conditions are met, the process 1000 may proceed from the step 1004 to a pre-converge condition monitoring step 1006. In some embodiments, if one or more of the initial conditions are not met, the process 1000 may proceed from the step 1004 back to the initial condition monitoring step 1002.

In some embodiments, the initial conditions may include one or more of (i) whether a first threshold amount of time (e.g., 30 days) has passed since implantation or insertion of the sensor 100, (ii) whether a second threshold amount of time (e.g., 10 days) has passed since the last parameter adjustment, (iii) whether no parameter adjustment has been performed since the sensor 100 was implanted or inserted, (iv) whether a new transceiver link process to link the sensor 100 to a new or replacement transceiver 101 has occurred, and (v) whether a calculation of responsivity (e.g., the responsiveness of the analyte indicator 106 of the sensor 100 to changes in analyte concentration) is below a responsivity threshold. In some non-limiting embodiments, the process 1000 may proceed from step 1004 to a pre-converge condition monitoring step 1106 if (1) the first threshold amount of time passed since implantation or insertion of the sensor 100, (2) a second threshold amount of time has passed since the last parameter adjustment, no parameter adjustment has been performed since the sensor 100 was implanted or inserted, or a new transceiver link process has occurred, and (3) the responsivity calculation is below the responsivity threshold.

In some non-limiting embodiments, calculating responsivity may include pairing calibration points with their closest sensor measurement. In some non-limiting embodiments, calculating responsivity may include correcting the SigOnOff_nA to 37 C (termed as SigOnOff_sensor_37C) using a temperature correction term. In some non-limiting embodiments, the SigOnOff_nA may be the digitized output of the signal photodetector 224, which is sensitive to emission light 331 from the indicator molecules 104 of the analyte indicator 106. In some non-limiting embodiments, the temperature correction term may be, for example and without limitation, 0.02. In some non-limiting embodiments, the temperature correction term may be within a range from 0-100%, and this range should be understood as describing and disclosing all temperature correction term values (including all decimal or fractional values) and sub-ranges within this range. In some non-limiting embodiments, calculating responsivity may include calculating the "supposed" SigOnOff_nA at manufacturing testing (termed as SigOnOff_QC) through the inverse kd equation. In some embodiments, the inverse kd equation is the G=kd*(s−smin)/(smax−s) equation flipped around to solve for s. In some embodiments, the responsivity may be defined as the ratio of the standard deviation of the two signals:

responsivity=std(SigOnOff_sensor_37C)/std(SigOnOff_QC).

In some embodiments, the responsivity threshold may be, for example and without limitation, 0.7. However, this is not required, and alternative embodiments may use different values for the responsivity threshold.

In some embodiments, the adjustment process 1000 may include a pre-converge condition monitoring step 1006 in which the transceiver 101 monitors one or more pre-converge conditions. In some embodiments, the adjustment process 1000 may include a step 1008 in which the transceiver 101 determines whether one or more pre-converge conditions are met. In some embodiments, if one or more of the pre-converge conditions are met, the process 1000 may proceed from the step 1008 to a gain converge step 1010. In some embodiments, if one or more of the pre-converge conditions are not met, the process 1000 may proceed from the step 1008 back to the pre-converge condition monitoring step 1006.

In some embodiments, the pre-converge conditions may include one or more of (i) whether a level of the transceiver battery 908 is above a battery threshold (e.g., 50%), (ii) whether an analyte rate of change level is below an analyte rate of change threshold (e.g., ±2 [mg/dL/min]), (iii) whether the analyte levels are within an analyte level range (e.g., between 100-200 [mg/dL]), (iv) whether the rate of change of the temperature of the sensor 100 (e.g., as measured by the temperature transducer 670) is below a temperature rate of change threshold (e.g., ±0.05 [C°/min]), (v) whether the temperature of the sensor 100 (e.g., as measured by the temperature transducer 670) is within a temperature range (e.g., 32-35 [C°/min]), (vi) whether the transceiver time is within a time range (e.g., between 07:00 and 20:00), and (vii) whether there were no ambient light alarms during the past hour and no active ambient light alarms. In some non-limiting embodiments, the process 1000 may proceed from step 1008 to a gain converge step 1010 if (1) the level of the transceiver battery 908 is above the battery threshold, (2) the analyte rate of change level is below the analyte rate of change threshold, (3) the analyte levels are within the analyte level range, (4) the rate of change of the temperature of the sensor 100 is below the temperature rate of change threshold, (5) the temperature of the sensor 100 is within the temperature range, (6) the transceiver time is within the time range, and (7) there were no ambient light alarms during the past hour and are no active ambient light alarms.

In some embodiments, the adjustment process 1000 may include a gain converge step 1010 in which the transceiver 101 converges on a new gain for the amplifier 111 and/or converges on a new drive current for the light source 108. In some non-limiting embodiments, the transceiver 101 may converge on the new values by projecting a signal level when using higher gain (and/or updated drive current) by using the current ADC and responsivity levels. In some embodiments, by using the following formula, the transceiver 101 may verify that the denominator result is not larger than a threshold (e.g., 2^11):

$$\frac{fmax - fmin}{(LED_{Current} * \text{Gain}) * (\text{modulation}_{eff}) - 1}$$

In some embodiments, the gain converge step 1010 may automatically converge on a higher gain than the current gain. In some embodiments, the new gain may be determined such that it will not saturate the ADC Sig On signal, considering that the temperature of the sensor 100 can reach 26° C. and 420 [mg/dL]. In some embodiments, the gain converge step 1010 may include the transceiver 101 saving the new gain setting for further use by a calibration buffer sequence.

In some embodiments, the adjustment process 1000 may include a step 1012 in which the transceiver 101 determines whether the gain converge step 1110 converged properly on one or more of a new gain for the amplifier 101 and a new drive current for the light source 108. In some non-limiting embodiments, the transceiver 101 may determine that the gain converge step 1110 converged properly if the determined gain or determined drive current is within a respective allowable range. If the converge was successful, the process 1000 may proceed from step 1012 to a calibration buffer building step 1014. If the converge was not successful, the process 1000 may proceed from step 1012 to a retry allowed determination step 1018.

In some embodiments, the adjustment process 1000 may include a calibration buffer building step 1014 in which the transceiver 101, for each reference or calibration point (e.g., SMBG value such as, for example, a finger stick) received by the transceiver 101, the transceiver 101 measures the ADC Sig On level for the current gain and for the gain found by the gain converge step 1010. In some embodiments, the calibration buffer building step 1014 may additionally or alternatively include, for each calibration point received by the transceiver 101, measuring the ADC Sig On level for the current drive current for the light source 108 and for the drive current found by the gain converge step 1010. In some non-limiting embodiments, the transceiver 101 may switch one or more of the amplifier gain and the drive current back and forth between the current and new values (e.g., by transmitting the new value(s) to the analyte sensor 100). In some embodiments, in step 1014, the transceiver 101 may build a buffer including a number (e.g., 5) of calibration points and their related ADC Sig On levels. In some non-limiting embodiments, the calibration points used for building the buffer may be only accepted calibration points (e.g., calibration points within an expected range).

In some embodiments, the adjustment process 1000 may include a gain change step 1016 in which the transceiver 101, after filling the calibration buffer in step 1014, changes one or more of the Sig On Gain for the amplifier 111 and the drive current for the light source 118 to the new value(s) calculated by gain converge step 1010. In some embodiments, the transceiver 101 may change one or more of the gain of the amplifier 111 and the drive current of the light source 108 conveying one or more of a new value of the gain of the amplifier 111 and a new value for the drive current of the light source 108. In some non-limiting embodiments, transceiver 101 may convey the new value(s) as part of, with, following, or preceding a change parameter command. In some non-limiting embodiments, the analyte sensor 100 may be configured to receive the new value(s) and update one or more of the gain of the amplifier 111 and the drive current of the light source 108. In some embodiments, the gain change step 1016 may include using the calibration buffer to update all calibration parameters, as if the analyte monitoring system 105 has gone through initialization.

Embodiments of the present invention have been fully described above with reference to the drawing figures. Although the invention has been described based upon these preferred embodiments, it would be apparent to those of skill in the art that certain modifications, variations, and alternative constructions could be made to the described embodiments within the spirit and scope of the invention. For instance, although aspects of the invention have been described above with respect to updating one or more of the amplifier gain and the light source drive current, in some alternative embodiments, the analyte monitoring system 50 additionally or alternative update one or more different parameters, which may include for example and without limitation one or more of the following parameters: the change in threshold for fluorescent signal, the baseline noise threshold, the change in expectation of accuracy, and the change in the baseline current. In some alternative embodiments, the analyte monitoring system 50 may dynamically change one or more parameters on the receiver side of the optical signal, one or more parameters on the driver side of the optical signal, or parameters on both the receiver and driver sides of the optical signal. In addition, although aspects of the invention have been described above with respect to updating parameters in an analyte monitoring system, in some alternative embodiments, parameter updating of the present invention may be applied to different devices (e.g., a temperature sensor, an insulin pump, or a pacemaker) in different systems (e.g., temperature monitoring systems, insulin delivery systems, or cardiac contraction control systems).

Aspects of the invention may additionally or alternatively relate to oxidation activated florescent molecules. In some non-limiting embodiments, the motivation for this patent may be to counteract the loss of active florescent molecules. In some embodiments, covering or locking the molecules using an oxidation sensitive molecule, may result in one or more of (i) before oxidation, the covering molecule blocking analyte from binding to the fluorescent molecule and, in addition, protects the fluorescent molecule from oxidation, and (ii) due to oxidation, the covering molecule detaching from the fluorescent molecule and, hence, activating it. In some embodiments, the oxidation activated florescent molecules may result in one or more of the following effects: (i) more stable modulation levels, which may contribute to accuracy, longevity, and needed calibration frequency, (ii) allowing patient specific oxidative compensation, which, for fast degrading patients, fast activation of active molecules would occur, and (iii) the addition of more complex molecules as well with stronger tenability to oxidation, adding modulation after substantial time since insertion, and/or oxidation of the once protected, released molecules, as well. In some embodiments, the oxidation activated florescent molecules may provide a self-repairing indicator/active sensing mechanism, which may be part of an analyte sensing system and may provide a prolonged use of a CGM.

Aspects of the invention may additionally or alternatively relate to a UV sensitive shield to protect a sensing layer of a secondary/multi sensing unit, which may be part of a dual/multi sensor CGM device. In some embodiments, the UV sensitive shield may extend the use of a dual sensor or multiple sensing-units CGM device by protecting the sensing unit from the interstitial fluid and activating it when necessary. In some embodiments, the activation may be by emitting UV light that dissolves the UV light-sensitive shield, exposing the active sensing layer to the interstitial fluid. In some embodiments, this activation may double the analyte sensor's lifetime. In some embodiments, the UV sensitive shield may provide delayed activation of sensing units as part of a CGM device for a prolonged use of a CGM device.

What is claimed is:

1. An analyte monitoring system comprising:
an analyte sensor including:

an indicator configured to exhibit one or more detectable properties based on an amount or concentration of an analyte in proximity to the indicator, a detector configured to detect one or more of the detectable properties and output an analyte signal indicative of the amount or concentration of the analyte in proximity to the indicator, and an amplifier configured to amplify the analyte signal; and a transceiver configured to:

determine whether one or more initial conditions are met, wherein determining whether the one or more initial conditions are met includes calculating a responsivity and determining whether the calculated responsivity is below a responsivity threshold; and adjust a gain of the amplifier.

2. The analyte monitoring system of claim 1, wherein the analyte sensor further comprises an analog-to-digital converter (ADC) configured to quantize the amplified analyte signal.

3. The analyte monitoring system of claim 1, wherein adjusting the gain of the amplifier comprises increasing the gain of the amplifier.

4. The analyte monitoring system of claim 1, wherein the analyte sensor further comprises a light source configured to irradiate the indicator with excitation light.

5. The analyte monitoring system of claim 4, wherein the transceiver is further configured to adjust a drive current of the light source.

6. The analyte monitoring system of claim 1, wherein the responsivity is the responsiveness of the indicator of the analyte sensor to changes in the amount or concentration of the analyte in proximity to the indicator.

7. The analyte monitoring system of claim 1, wherein determining whether the one or more initial conditions are met further includes determining one or more of (i) whether a first threshold amount of time has passed since implantation or insertion of the analyte sensor, (ii) whether a second threshold amount of time has passed since a previous adjustment of the gain of the amplifier, and (iii) whether the gain of the amplifier has not been adjusted since the analyte sensor was implanted or inserted.

8. The analyte monitoring system of claim 7, wherein the transceiver is further configured to determine that the one or more initial conditions are met if the transceiver determines that (1) the first threshold amount of time has passed since implantation or insertion of the analyte sensor, (2) the gain of the amplifier has not been adjusted since the analyte sensor was implanted or inserted or the second threshold amount of time has passed since the previous adjustment of the gain of the amplifier, and (3) the calculated responsivity is below the responsivity threshold.

9. The analyte monitoring system of claim 1, wherein adjusting the gain of the amplifier comprises:

calculating a new gain for the amplifier of the analyte sensor; and changing the gain of the amplifier to the calculated new gain.

10. The analyte monitoring system of claim 1, wherein the transceiver is further configured to, if the transceiver determines that the one or more initial conditions are met, determine whether one or more pre-converge conditions are met.

11. An analyte monitoring system comprising:
an analyte sensor including:

an indicator configured to exhibit one or more detectable properties based on an amount or concentration of an analyte in proximity to the indicator, a detector configured to detect one or more of the detectable properties and output an analyte signal indicative of the amount or concentration of the analyte in proximity to the indicator, and an amplifier configured to amplify the analyte signal; and a transceiver configured to:

determine whether one or more pre-converge conditions are met; and adjust a gain of the amplifier.

12. The analyte monitoring system of claim 11, wherein the transceiver is further configured to determine whether one or more initial conditions are met.

13. The analyte monitoring system of claim 12, wherein determining whether the one or more initial conditions are met includes calculating a responsivity and determining whether the calculated responsivity is below a responsivity threshold.

14. The analyte monitoring system of claim 12, wherein the transceiver is further configured to, if the transceiver determines that the one or more initial conditions are met, determine whether the one or more pre-converge conditions are met.

15. The analyte monitoring system of claim 11, wherein determining whether the one or more pre-converge conditions are met includes determining one or more of (i) whether a level of a battery of the transceiver is above a battery threshold, (ii) whether a rate of change of the amount or concentration of the analyte in proximity to the indicator is below an analyte rate of change threshold, (iii) whether the amount or concentration of the analyte in proximity to the indicator is within an analyte level range, (iv) whether a rate of change of a temperature of the analyte sensor is below a temperature rate of change threshold, (v) whether the temperature of the analyte sensor is within a temperature range, (vi) whether a time of the transceiver is within a time range, (vii) whether there were any ambient light alarms during the past hour, and (viii) whether there are any active ambient light alarms.

16. The analyte monitoring system of claim 15, wherein the transceiver is further configured to determine that the one or more pre-converge conditions are met if the transceiver determines that (i) the level of the battery of the transceiver is above the battery threshold, (ii) the rate of change of the amount or concentration of the analyte in proximity to the indicator is below the analyte rate of change threshold, (iii) the amount or concentration of the analyte in proximity to the indicator is within the analyte level range, (iv) the rate of change of the temperature of the analyte sensor is below the temperature rate of change threshold, (v) the temperature of the analyte sensor is within the temperature range, (vi) the time of the transceiver is within the time range, (vii) there were no ambient light alarms during the past hour, and (viii) there are no active ambient light alarms.

17. The analyte monitoring system of claim 11, wherein the transceiver is further configured to adjust the gain of the amplifier only if the transceiver determines that the one or more pre-converge conditions are met.

18. The analyte monitoring system of claim 11, wherein adjusting the gain of the amplifier comprises:

calculating a new gain for the amplifier of the analyte sensor; and changing the gain of the amplifier to the calculated new gain.

19. An analyte monitoring system comprising:
an analyte sensor including:
an indicator configured to exhibit one or more detectable properties based on an amount or concentration of an analyte in proximity to the indicator,
a detector configured to detect one or more of the detectable properties and output an analyte signal indicative of the amount or concentration of the analyte in proximity to the indicator, and
an amplifier configured to amplify the analyte signal; and
a transceiver configured to adjust a gain of the amplifier, wherein adjusting the gain of the amplifier comprises:
calculating a new gain for the amplifier of the analyte sensor;
building a calibration buffer; and
changing the gain of the amplifier to the calculated new gain.

20. The analyte monitoring system of claim 19, wherein:
the analyte sensor further comprises an analog-to-digital converter (ADC) configured to quantize the amplified analyte signal;
the transceiver is further configured to receive one or more reference measurements;
building the calibration buffer comprises, for each of the one or more reference measurements, measuring an ADC Sig On level for the gain of the amplifier before changing to the calculated new gain and for the calculated new gain; and
the calibration buffer includes the one or more reference measurements and the measured ADC Sig On levels.

21. A method comprising:
using a detector of an analyte sensor to detect one or more detectable properties exhibited by an indicator of the analyte sensor based on an amount or concentration of an analyte in proximity to the indicator;
using an amplifier of the analyte sensor to amplify the analyte signal;
using a transceiver to determine whether one or more initial conditions are met, wherein determining whether the one or more initial conditions are met includes calculating a responsivity and determining whether the calculated responsivity is below a responsivity threshold; and
using the transceiver to adjust a gain of the amplifier.

22. The method of claim 21, further comprising using an analog-to-digital converter (ADC) to quantize the amplified analyte signal.

23. The method of claim 21, wherein adjusting the gain of the amplifier comprises increasing the gain of the amplifier.

24. The method of claim 21, further comprising using the transceiver to adjust a drive current of a light source of the analyte sensor.

25. The method of claim 21, wherein the responsivity is the responsiveness of the indicator of the analyte sensor to changes in the amount or concentration of the analyte in proximity to the indicator.

26. The method of claim 21, wherein determining whether the one or more initial conditions are met further includes determining one or more of (i) whether a first threshold amount of time has passed since implantation or insertion of the analyte sensor, (ii) whether a second threshold amount of time has passed since a previous adjustment of the gain of the amplifier, and (iii) whether the gain of the amplifier has not been adjusted since the analyte sensor was implanted or inserted.

27. The method of claim 26, wherein the transceiver determines that the one or more initial conditions are met if the transceiver determines that (1) the first threshold amount of time has passed since implantation or insertion of the analyte sensor, (2) the gain of the amplifier has not been adjusted since the analyte sensor was implanted or inserted or the second threshold amount of time has passed since the previous adjustment of the gain of the amplifier, and (3) the calculated responsivity is below the responsivity threshold.

28. The method of claim 21, wherein adjusting the gain of the amplifier comprises:
calculating a new gain for the amplifier of the analyte sensor; and
changing the gain of the amplifier to the calculated new gain.

29. The method of claim 21, further comprising using the transceiver to, if the transceiver determines that the one or more initial conditions are met, determine whether one or more pre-converge conditions are met.

30. A method comprising:
using a detector of an analyte sensor to detect one or more detectable properties exhibited by an indicator of the analyte sensor based on an amount or concentration of an analyte in proximity to the indicator;
using an amplifier of the analyte sensor to amplify the analyte signal;
using a transceiver to determine whether one or more pre-converge conditions are met; and
using the transceiver to adjust a gain of the amplifier.

31. The method of claim 30, further comprising using the transceiver to determine whether one or more initial conditions are met.

32. The method of claim 31, wherein determining whether the one or more initial conditions are met includes calculating a responsivity and determining whether the calculated responsivity is below a responsivity threshold.

33. The method of claim 31, further comprising using the transceiver to, if the transceiver determines that the one or more initial conditions are met, determine whether the one or more pre-converge conditions are met.

34. The method of claim 30, wherein determining whether the one or more pre-converge conditions are met includes determining one or more of (i) whether a level of a battery of the transceiver is above a battery threshold, (ii) whether a rate of change of the amount or concentration of the analyte in proximity to the indicator is below an analyte rate of change threshold, (iii) whether the amount or concentration of the analyte in proximity to the indicator is within an analyte level range, (iv) whether a rate of change of a temperature of the analyte sensor is below a temperature rate of change threshold, (v) whether the temperature of the analyte sensor is within a temperature range, (vi) whether a time of the transceiver is within a time range, (vii) whether there were any ambient light alarms during the past hour, and (viii) whether there are any active ambient light alarms.

35. The method of claim 34, wherein the transceiver determines that the one or more pre-converge conditions are met if the transceiver determines that (i) the level of the battery of the transceiver is above the battery threshold, (ii) the rate of change of the amount or concentration of the analyte in proximity to the indicator is below the analyte rate of change threshold, (iii) the amount or concentration of the analyte in proximity to the indicator is within the analyte level range, (iv) the rate of change of the temperature of the analyte sensor is below the temperature rate of change threshold, (v) the temperature of the analyte sensor is within the temperature range, (vi) the time of the transceiver is within the time range, (vii) there were no ambient light alarms during the past hour, and (viii) there are no active ambient light alarms.

36. The method of claim 30, further comprising using the transceiver to adjust the gain of the amplifier only if the transceiver determines that the one or more pre-converge conditions are met.

37. The method of claim 30, wherein adjusting the gain of the amplifier comprises:
calculating a new gain for the amplifier of the analyte sensor; and
changing the gain of the amplifier to the calculated new gain.

38. A method comprising:
using a detector of an analyte sensor to detect one or more detectable properties exhibited by an indicator of the analyte sensor based on an amount or concentration of an analyte in proximity to the indicator;
using an amplifier of the analyte sensor to amplify the analyte signal; and
using the transceiver to adjust a gain of the amplifier, wherein adjusting the gain of the amplifier comprises:
calculating a new gain for the amplifier of the analyte sensor;
building a calibration buffer; and
changing the gain of the amplifier to the calculated new gain.

39. The method of claim 38, further comprising:
using an analog-to-digital converter (ADC) of the analyte sensor to quantize the amplified analyte signal; and
using the transceiver to receive one or more reference measurements;
wherein building the calibration buffer comprises, for each of the one or more reference measurements, measuring an ADC Sig On level for the gain of the amplifier before changing to the calculated new gain and for the calculated new gain; and
wherein the calibration buffer includes the one or more reference measurements and the measured ADC Sig On levels.

* * * * *